United States Patent [19]
Davidow

[11] Patent Number: 5,679,538
[45] Date of Patent: Oct. 21, 1997

[54] METHOD FOR USING LEAD-SENSITIVE ENZYMES TO DETERMINE LEVELS OF LEAD IN BLOOD AND OTHER TYPES OF SAMPLES

[76] Inventor: Bernard Davidow, 153-24 Booth Memorial Ave., Flushing, N.Y. 11355

[21] Appl. No.: 200,052

[22] Filed: Feb. 22, 1994

[51] Int. Cl.$^6$ .............................. C12Q 1/34; G01N 33/20
[52] U.S. Cl. .............................. 435/18; 436/74; 436/815
[58] Field of Search .............................. 435/18, 7.71, 7.91, 435/808; 436/63, 74, 171, 172, 815

[56] References Cited

U.S. PATENT DOCUMENTS 3,973,129 8/1976 Blumberg .............................. 250/461 B

OTHER PUBLICATIONS

Witting U., Evaluation Of A New Specific Analysis . . . Int Arch Occup Environ Health 1987 59:375–383.
Verebey R., Rapid Sensitive Micro Blood Lead Analysis . . . J Of Anal Toxicology vol. 15 Sep./Oct. 1991, pp. 237–240.

*Primary Examiner*—Ralph Gitomer
*Attorney, Agent, or Firm*—Meislik & Levavy

[57] ABSTRACT

A method is described for determining the level of lead in blood and other types of samples. The level of lead is determined by using a lead-sensitive enzyme. As a first step, a native lead-sensitive enzyme in the sample is disabled. This step may be omitted if the sample is known not to contain any lead-sensitive enzymes. A quantity of lead-sensitive enzyme with known enzymatic activity is then added to the sample. The new enzymatic activity of the sample is then measured. Finally, the level of lead in the sample is determined from the measurement of the new enzymatic activity, which differs from the known enzymatic activity if lead is present in the sample.

22 Claims, 1 Drawing Sheet

METHOD FOR USING LEAD-SENSITIVE ENZYMES TO DETERMINE LEVELS OF LEAD IN BLOOD AND OTHER TYPES OF SAMPLES

FIELD OF THE INVENTION

The present invention encompasses a method for using lead-sensitive enzymes to determine the level of lead in various samples. The present invention has particular application in testing for lead in blood samples.

BACKGROUND OF THE INVENTION

Several enzymes function as indicators for the detection of blood lead levels in the body. In particular, the enzyme δ-aminolevulinic acid dehydratase (δ-ALAD) (also known as porphobilinoen synthase (PBGS)) is known to be an extremely sensitive indicator for the detection of blood lead levels in the body (Hernberg S., et al., δ-ALAD as a measure of lead exposure, Arch. Environ. Hlth., 21: 140–145, 1970). The enzyme is a catalyst in the second order reaction in the heme synthesis pathway, converting 2 mol of δ-aminolevulinic acid (δ-ALA) into 1 mol of porphobilinogen (Kappas, A., Sassa, S., et al., The Porphyrias. The Metabolic Basis of Inherited Disease, 5th ed., J. B. Stanbury et al., eds. McGraw Hill, N.Y. pp. 1301–1384, 1983). The enzymatic activity is seen to be reduced by the presence of lead (DeBruin, A., Effect of lead exposure on the level of δ-ALAD activity, Med. Lavoro, 59: 411–418, 1968).

The inactivation can be reversed by the addition of zinc (Border, E. A., et al., The in-vitro effect of Zn on the inhibition of δ-ALAD, Br. Jr. Ind. Med., 33: 85–87, 1976) or dithiothreitol (DA), or by heating (Sakai, T., Yamaghira, S., Ushio, K., Restoration of lead inhibited δ-ALAD activity in whole blood by heat, zinc and/or dithiothreitol, Clin. Chem. 26: 625–628, 1980).

These findings have resulted in a standardized approach for the study of lead exposure by the inhibition of δ-ALAD activity in whole blood. The European Standardized δ-ALAD Assay (Berlin, A., Schaller-K. H., European standardized method for the determination of δ-ALAD activity in blood, Z. Klin. Chem. Klin. Biochim, 12: 339–390, 1974) is based on the incubation of the enzyme in the sample with an excess of δ-ALA the substrate; the porphobilinogen formed is reacted with modified Ehrlich's reagent to form a chromophore which is assayed in a spectrophotometer to obtain a direct measure of δ-ALAD activity.

The direct assay was modified to measure the ratios of enzyme activity before and after activation with dithiothreitol (Granick, J. L., Sassa, S., Granick, S., et al., Studies in lead poisoning II: Correlation between ratio of activated to inactivated δALAD activity determination, Int. Arch. Occup. Hlth., 39: 135–141, 1977) as a more reliable measure of lead absorption particularly among children who are the most susceptible group to lead poisoning (Chisolm, J. J. Jr., Thomas, D. J., Hamill, T. G., Erythrocyte Porphobilinogen Synthase Activity as an indicator of lead exposure in children, Clin. Chem., 31, 4, 601–605, 1985).

The current standard methods to measure lead induced δ-ALAD inhibition suffer from several drawbacks that severely limit the assay as an epidemiological tool for mass screening. The direct methods such as the European Standard Method or the ratios of activated to inactivated δ-ALAD method require immediate determinations as there is a significant drop in enzyme activity even upon storage at 4° C. To maintain optimal enzyme activity investigators such as Chisolm et. al., collect and store blood at −70° C. while other investigators have used heating at 60° C. for reactivation (Trevisan, A., Raimondi, M., Bungaro, A., Chiesura, P., Heating reactivation of rat δ-ALAD in lead poisoning, Sci. Total Environ., 71: 547–550, 1980). The collection and processing of samples by any of the conventional δ-ALAD assays requires highly specialized equipment and handling that is unsuitable for mass screening.

Another inherent drawback of the current δ-ALAD assay schemes is revealed in the work by Battistuzzi (Battistuzzi, G., et al., δ-ALAD: a new genetic polymorphism in man, Ann. Human Genetics, 45: 223–229, 1981) and Benkmann (Benkmann, H. G., et. al., Polymorphism of δ-ALAD in various populations, Human Heredity, 33: 62–64, 1983) that shows that genetic polymorphism of δ-ALAD and the resulting differences in sensitivity may account for some of the unexplained susceptibility to lead among certain children (Rogan, W. J., Reigart, J. R., Gladden, B. C., Association of δ-ALAD levels and ferrochelatase inhibition in childhood lead exposure, J. Pediatrics, 109: 60–63, 1986) in large population groups. The current methods that rely on measuring the blood lead ("Pb-B") induced inactivation of δ-ALAD naturally present in the red blood cells, do not take into account the special effect due to polymorphorism that may lead to erroneous results among individuals.

Lead inhibition of the activity of enzymes other than δ-ALAD has also been shown. These other enzymes therefore can operate as indicators for levels of lead in blood. For example, investigators have shown that erythrocyte pyrimidine 5'-nucleotidase (P5N) exhibits lead detecting capabilities. (Tomokuni, K. and Ichiba, M., Comparison of inhibition of erythrocyte pyrimidine 5'-nucleotidase and δ-aminolevulinic acid dehydratase by lead, Toxicology Letters, 40: 159–163, 1988)

OBJECTS AND SUMMARY OF THE INVENTION

An object of the present invention is to offer a simple, inexpensive, and efficient technique for mass screening for low levels of lead in blood using lead-sensitive enzymes in an improved method that reduces the need for elaborate blood sample collection and storage.

Another object of the present invention is to make the determination or measurement of lead in blood a simple and precise test that reduces significant polymorphic variations.

Another object of the present invention is to provide a method for the determination or measurement of lead not limited to blood samples.

The present invention provides an enzyme method for the determination of lead levels in blood, comprising the following steps: (A) disabling a native lead-sensitive enzyme in a blood sample; (B) adding a selected amount of a lead-sensitive enzyme such as delta-aminolevulinic acid dehydratase of known enzymatic activity to said sample, where said added enzyme is added along with an activating or protecting agent; (C) measuring the enzymatic activity of said added enzyme in said sample; and (D) calculating the amount of lead in said sample based on the measurement of enzymatic activity as compared with standards containing known amounts of lead and treated in similar fashion.

The present invention has the advantage that there is no need to protect the native lead-sensitive enzyme in a sample, since it is to be disabled anyway. The present invention therefore does not require elaborate storage and cooling mechanisms for blood samples. Furthermore, the present invention reduces worries about genetic variations when testing for the level of lead in blood samples.

DETAILED DESCRIPTION

Figure 1:
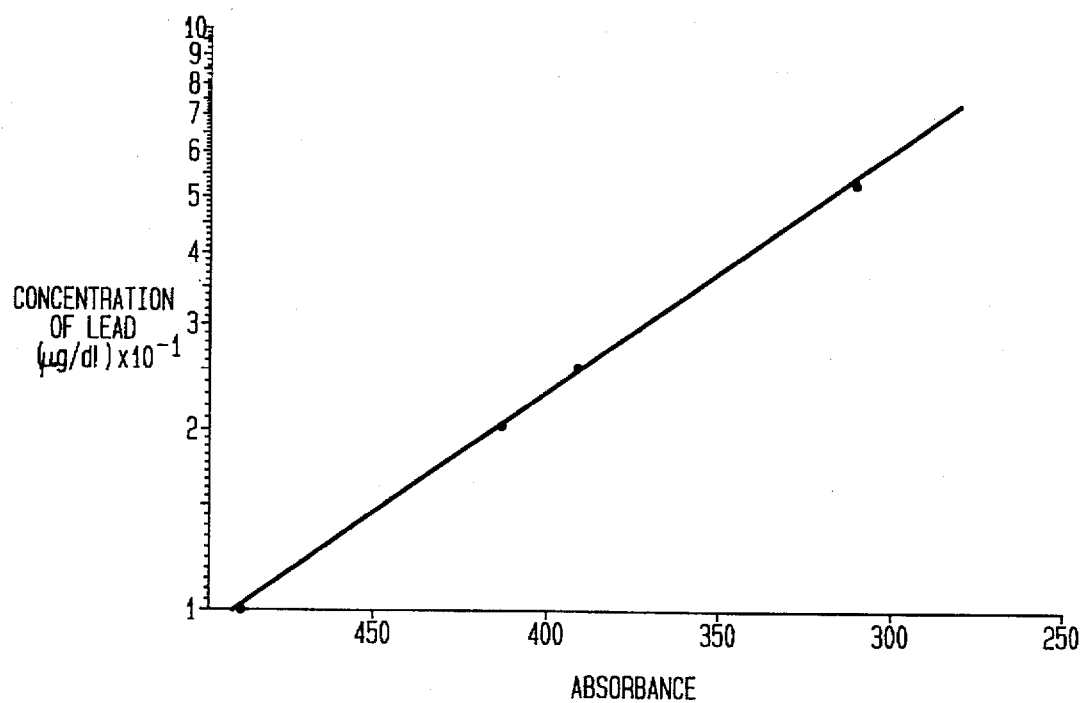
FIG. 1 shows the plot of a typical concentration curve used in Example 1 below to determine the level of lead from a chromophore.

Blood Sample Testing Using Delta-Aminolevulinic Acid Dehydratase

As a first step the δ-ALAD enzyme native to a blood sample is disabled. The enzyme can be disabled by a variety of methods. One simple method is to heat the blood sample to a temperature high enough to disable the native enzyme. This can be accomplished by heating the sample in a boiling water bath (i.e., at 100° C.). (The sample may be heated using lower temperatures, as long as the enzyme is disabled.) The enzyme may be disabled by other methods as well, including by microwave radiation or high intensity ultraviolet radiation, or by exposure to acids.

The sample is then equilibrated at a known pH level with an aliquot of δ-ALAD enzyme of known specific activity. To provide an adequate δ-ALAD activity level for measurement, the pH level should be in the range of pH 5–pH 7.(The point of optimal enzyme activity for δ-ALAD is pH 6.4.)

The specific activity is maintained by activating or protecting the enzyme with dithiothreitol (DTT), zinc, or other known materials. The ratio of the enzyme to the protecting agent should be enough to maintain the enzyme activity but should not interfere with the inhibition by the lead in the sample. DTT has been found to function well in this capacity.

After the addition of the new amount of δ-ALAD, the enzyme activity is inhibited in proportion to the lead in the blood sample. Thus the level of lead in the sample can be measured by determining the remaining enzyme activity. The remaining enzyme activity is determined by incubation at an appropriate temperature with a known amount of δ-ALAD (δ-aminolevulinic acid) for a length of time appropriate to convert the substrate to porphobilinogen. The lower the temperature, the longer the length of time for the substrate to be converted to porphobilinogen. At 37° C., the minimum length of time required for adequate incubation is about 15 minutes. The preferred length of time for incubation at 37° C. is about 30 minutes. However, the sample should be incubated longer at lower temperatures.

After the desired time the same solution is treated with a suitable reagent to precipitate out the proteins. This essentially stops the reaction that forms the porphobilinogen. An example of a suitable reagent is trichloroacetic acid/ mercuric chloride. The solution is then centrifuged, separating the clarified liquid part and the precipitate.

The porphobilinogen remains in the clarified liquid part. This liquid part is separated out by pipetting or by any other conventional method. One alternate method is to use disposable filtration units of a pore size around 0.45μ to enhance the clarification.

The porphobilinogen in the clarified layer is reacted with any known color reagent to form a chromophore. As an example, Ehrlich's solution can be reacted with the porphobilinogen to form a chromophore.

The chromophore is then assayed in a spectrophotometer to determine the level of porphobilinogen formed. A wavelength between 550 nm and 560 nm is optimal for assaying the Ehrlich's chromophore.

The level of porphobilinogen formed is used to calculate the enzyme activity by the standard methods of calculation described in the literature to obtain the level of lead present in the blood sample. See, e.g., The European Standardized δ-ALAD Assay (Berlin, A., Schaller K. H., European standardized method for the determination of δ-ALAD activity in blood, Z. Klin. Chem. Klin. Biochim., 12: 339–390, 1974).

The technique described above is sufficient to measure as little as 0.50 nanogram of lead in a 10 μL sample. Using a 10 μL aliquot of sample this level of detection corresponds to 5 μg/dL Pb-B. This level is well below the cutoff limit of 10 μg/dL promulgated by the Federal Center for Disease Control in 1991.

The technique described above can also be used to assay lead levels in dried blood spots on filter paper. The enzyme native to the blood is disabled and the spot is equilibrated and incubated by the method described above.

The assay steps described above are carried out in ordinary lab test tubes essentially free from metal contaminants and can be centrifuged in batches. If the filtration procedure is used to effect clarification it requires individual disposable filters. The chromophore can by assayed using an ordinary lab spectrophotometer, or a more advanced unit fitted with a flow cell and an auto-sampler. The process can also be automated with laboratory robotic units. Alternatively, mass screening can be effected by mixing the clarified sample with modified Ehrlich solution in a microtiter plate to be read in a plate reader. The following examples are detailed descriptions of each mode of use described above.

EXAMPLE 1

This example describes the technique of the present invention for the determination of lead levels in whole blood wherein the assay is performed using 96 well microtiter plates and a plate reader. The example also illustrates the balance required between the concentrations of the δ-ALAD enzyme and its activating or protecting agent, dithiothreitol (DTT), for the analysis.

The various steps in the analytical procedure are as follows: a sample of whole blood (20 μL) is added to 230 μL of an appropriate buffer at pH 6.4 in acid washed glass or plastic tubes and heated in boiling water for 5 minutes. This step disables the δ-ALAD enzyme native to the sample. The order of this step is unimportant, i.e. the buffer can be added after the enzyme is disabled.

The contents are allowed to cool to room temperature (or warmer, but not warm enough to disable any newly added Δ-ALAD) and mixed with 50 μL of δ-ALAD/DTT mixture and equilibrated in a 37° C. water bath for at least 15 minutes. This step inactivates the enzyme in proportion to the amount of lead present in the sample.

The remaining enzyme activity is measured by adding 200 μL of δ-ALA (δ-aminolevulinic acid: 16.76 mg/20 mL pH 6.4 buffer) which is converted proportionately to porphobilinogen (2 mol δ-ALA to 1 mol PBG). The protein content of the mixture is precipitated using 100 μL mercuric chloride/trichloroacetic acid (1.35 grams $HgCl_2$ in 100 mL of 0.1% solution of TCA). The tubes are centrifuged at 5000 rpm for 10 minutes. 200 μL of the clear supernatant is then pipetted into the assigned well of the microtiter plate. After the desired number of samples have been pipetted into the plate, 200 μL of modified Ehrlich solution is added to each. (The Ehrlich solution is prepared by adding 21 ml of p-DMAB solution—para dimethyl amino benzaldehyde 2.5 g/50 mL glacial acetic acid—with 4 mL perchloric acid.) It is necessary to add the Ehrlich's solution to all the samples in the microtiter plate at the same time so that the chromophore development occurs for the same time in each case. After 10 minutes to allow for color development, the plate is read at a wavelength of 555 nm. The amount of lead in each sample is calculated from a concentration curve plotted for each plate by comparing the amount of chromophore produced with a set of standards containing known amounts of lead and treated identically.

FIG. 1 shows the plot of a typical concentration curve obtained with the above procedure. The range of concentration shown corresponds to 10 to 50 µg/100 mL blood. The range can be altered as desired by changing the volumes of some of the various components proportionately.

To determine the desired proportions of the δ-ALAD enzyme and DTT activator a series of experiments were carried out. The procedure was essentially the same as that described above with two adjustments. The enzyme and the DTT were prepared as separate solutions. The δ-ALAD enzyme lot was assayed as 3 mg/mL protein content that was diluted to yield a concentration of 7.5 µg in 25 µL pH 6.4 buffer. The DTT solution was prepared to give a concentration of 30.9 mg/400 mL buffer. Three sets of concentration curves were prepared using the same amount of enzyme and 10, 25, 50 µL of DTT. The experimental data showed that 10 µL DTT was insufficient, 25µL gave readings that could be plotted but had low sensitivity while 50 µL gave the best results. The enzyme solution for the assay procedure described in this example was prepared with the ratios ascertained by this experiment. It must be pointed out that once the enzyme concentration is known the DTT ratio can be mathematically determined based upon the initial study.

EXAMPLE 2

This example illustrates how the technique of the present invention could be used for the assay of lead levels in blood spots dried on filter discs. The filters in this example have special features that allow uniform absorption of blood over its surface which can then be punched out as 0.25" discs, corresponding to 10 µL of whole blood. The disc can be soaked in pH 6.4 buffer and vortexed or sonicated. The enzyme native to the blood sample can be disabled by exposure to a high intensity UV light. Alternatively, the enzyme can be disabled by microwave radiation or boiling water as described in Example 1. The assay then can follow the same steps that are described in Example 1. To maintain the same levels of sensitivity the volume of the reagents described should be reduced by one half. The final volume of reagents then can be used in microtiter plates or spectrophotometers equipped with flow cells.

Non-Blood Sample Testing

Since the present invention does not rely upon naturally occurring lead-sensitive enzymes, the method described above is equally suitable for testing for levels of lead in samples other than blood.

For instance, δ-ALAD can be used in the above manner to test for lead in water samples. In fact, the procedure is less complicated, since water contains no native δ-ALAD. Therefore, the step described above for disabling δ-ALAD native to the sample (by heat, microwave, ultraviolet radiation, or exposure to acid) can be omitted. The method of the invention then proceeds as described in the blood sample case.

Use of Other Lead-Sensitive Enzymes

δ-ALAD, while one of the most sensitive of lead-sensitive enzymes, is not the only enzyme to exhibit lead detection capabilities. Therefore, the invention contemplates that other lead-sensitive enzymes could also be used in the manner described in the invention. Only the characteristics particular to the enzyme would need to be altered. For instance, the pH levels may be slightly different to provide optimal enzymatic activity for the particular lead-sensitive enzyme. As described in the Background of the Invention, erythrocyte pyrimidine 5'-nucleotidase can be used as an indicator for lead and, while not as sensitive as δ-ALAD, would be suitable to be used in the manner described by the present invention.

What is claimed is:

1. A method for determining a lead level in a blood sample, comprising the following steps:
   A. disabling a native lead-sensitive enzyme in said blood sample;
   B. activating an additional lead-sensitive enzyme having a known enzymatic activity thereby producing an activated additional lead-sensitive enzyme, wherein said additional lead-sensitive enzyme is delta-aminolevulinic acid dehydratase ("delta-ALAD"), by adding dithiothreitol ("DTT") as an activating or protecting agent to said additional lead-sensitive enzyme to activate said additional lead-sensitive enzyme, said activating step being performed separately from said disabling step A;
   C. adding an amount of said activated additional lead-sensitive enzyme to said blood sample, wherein said activated additional lead-sensitive enzyme is added along with said activating or protecting agent;
   D. measuring a measured enzymatic activity of said activated additional lead-sensitive enzyme; and
   E. determining said lead level by comparing said measured enzymatic activity to a standard measured enzymatic activity produced with a set of standards containing a known lead level and treated identically as said blood sample.

2. The method according to claim 1, wherein said native lead-sensitive enzyme is disabled by heat, microwave radiation, ultraviolet radiation, or exposure to acid.

3. The method according to claim 1, wherein said blood sample is adjusted to a pH level where said enzyme activity is optimized with a buffer.

4. The method according to claim 3, wherein said pH level is between 5.0 and 7.0.

5. The method according to claim 1, wherein said blood is human whole blood.

6. The method according to claim 5, wherein said measuring step further comprises the following steps:
   A. incubating said blood sample as a certain temperature between 15 degrees C. and 40 degrees C.;
   B. adding a known amount of delta-aminolevulinic acid to said blood sample;
   C. incubating said blood sample for a length of time between 15 minutes and 60 minutes;
   D. removing proteins from said blood sample to produce a test solution;
   E. reacting said test solution with a color reagent to form a chromophore;
   F. assaying said chromophore in a spectrophotometer; and
   G. measuring said measured enzymatic activity of said additional lead-sensitive enzyme by comparing a quantity of said chromophore to a standard quantity of chromophore produced with a set of standards containing a known lead level and treated identically as said blood sample.

7. The method according to claim 6, wherein said length of time is between 15 minutes and 30 minutes.

8. The method according to claim 6, wherein said removing step comprises precipitating and centrifuging said blood sample.

9. The method according to claim 8, wherein said precipitating comprises adding a reagent comprising mercuric chloride and trichloroacetic acid to said blood sample.

10. The method according to claim 6, wherein said removing step comprises filtering said blood sample.

11. The method according to claim 6, wherein said color reagent is modified Ehrlich's solution.

12. The method according to claim 11, wherein said spectrophotometer detects said chromophore at a wavelength of between 550 nm and 560 nm.

13. A method for determining a lead level in a sample with no native lead-sensitive enzymes, comprising the following steps:

A. activating a lead-sensitive enzyme having a known enzymatic activity, by adding dithiothreitol ("DTT") as an activating or protecting agent to said lead-sensitive enzyme to activate said lead-sensitive enzyme;

B. adding a known amount of said activated lead-sensitive enzyme to said sample, wherein said activated lead-sensitive enzyme is delta-aminolevulinic acid dehydratase ("delta-ALAD"), and said activated lead-sensitive enzyme is added along with said activating or protecting agent;

C. measuring a measured enzymatic activity of said activated lead-sensitive enzyme after said activated lead-sensitive enzyme has been added to said sample;

D. determining said lead level by comparing said measured enzymatic activity to a standard measured enzymatic activity produced with a set of standards containing a known lead level and treated identically as said sample.

14. The method according to claim 13, wherein said sample is adjusted to a pH level where said enzyme activity is optimized with a buffer.

15. The method according to claim 14, wherein said pH level is between 5.0 and 7.0.

16. The method according to claim 13, wherein said sample is water.

17. The method according to claim 13, wherein said measuring step further comprises the following steps:

A. incubating said sample at a temperature between 15 degrees C. and 40 degrees C.;

B. adding a known amount of delta-aminolevulinic acid to said sample;

C. incubating said sample for a length of time between 15 minutes and 60 minutes;

D. removing proteins from said sample to produce a test solution;

E. reacting said test solution with a color reagent to form a chromophore;

F. assaying said chromophore in a spectrophotometer; and

G. measuring said measured enzymatic activity of said lead-sensitive enzyme by comparing a quantity of said chromophore to a standard quantity of chromophore produced with a set of standards containing a known lead level and treated identically as said sample.

18. The method according to claim 17, wherein said length of time is between 15 minutes and 30 minutes.

19. The method according to claim 17, wherein said removing step comprises precipitating and centrifuging said sample.

20. The method according to claim 19, wherein said precipitating comprises adding a reagent comprising mercuric chloride and trichloroacetic acid to said sample.

21. The method according to claim 17, wherein said removing step comprises filtering said sample.

22. The method according to claim 17, wherein said color reagent is modified Ehrlich's solution and wherein said spectrophotometer detects said chromophore at a wavelength of between 550 nm and 560 nm.

* * * * *